United States Patent [19]
Erickson

[11] Patent Number: 5,300,226
[45] Date of Patent: * Apr. 5, 1994

[54] WASTE HANDLING METHOD

[75] Inventor: Stewart E. Erickson, Ketchum, Id.

[73] Assignee: Stewart E. Erickson Construction, Inc., Marietta, Pa.

[ * ] Notice: The portion of the term of this patent subsequent to Mar. 20, 2007 has been disclaimed.

[21] Appl. No.: 647,592

[22] Filed: Jan. 28, 1991

Related U.S. Application Data

[63] Continuation-in-part of Ser. No. 601,873, Oct. 23, 1990, Pat. No. 5,261,929.

[51] Int. Cl.$^5$ .................................. C02F 3/28
[52] U.S. Cl. ........................ 210/603; 210/747
[58] Field of Search ............ 210/603, 747, 631, 241; 220/1.5; 383/902

[56] References Cited

U.S. PATENT DOCUMENTS

| | | | |
|---|---|---|---|
| 2,875,562 | 3/1959 | Mitchell | 53/22 |
| 3,577,678 | 5/1971 | Burton | 210/603 |
| 3,831,792 | 8/1974 | Waterman et al. | 214/42 R |
| 4,204,842 | 5/1980 | Morel et al. | 210/603 |
| 4,497,259 | 2/1985 | Titterton | 105/359 |
| 4,579,654 | 4/1986 | Bremmer | 210/603 |
| 4,670,148 | 6/1987 | Schneider | 210/603 |
| 4,678,389 | 7/1987 | Bonerb et al. | 414/267 |
| 4,735,457 | 4/1988 | Bonerb et al. | 298/27 |
| 4,758,344 | 7/1988 | Wildenauer | 210/603 |
| 4,897,195 | 1/1991 | Erickson | 210/603 |
| 4,909,156 | 3/1990 | Erickson | 105/39 |

OTHER PUBLICATIONS

Brochure of Amfuel entitled "Fabribin ® cuts costs on shipping/handling/storage!".
Brochure of Uniroyal Sealdtank ® "Now . . . haul liquid lading in any dry bed".
An Introduction to Biogas Production on the Farm, The National Center for Appropriate Technology, U.S. Dept. of Energy, Contract No. DE-AC01-82CE15095, pub. Mar., 1984.
"Carbon Dioxide Fertilization", Chapter 9, which discusses the advantages of growing plants with an enhanced carbon dioxide concentration in a greenhouse environment.
Greenhouse Tomatoes, Lettuce and Cucumbers, "Cultural Requirements", pp. 190–203, S. Honma and S. H. Wittwer (1979).
Energy Sense (Spring 1985), "Biomass–Energy in the Future", pp. 20–22.
Penthouse (Jan. 1991), "Getting Wasted", Cool, Lisa C.

Primary Examiner—Thomas Wyse
Attorney, Agent, or Firm—Fredrikson & Byron

[57] ABSTRACT

A method of handling waste is disclosed. The invention includes providing a transport vehicle or the like having a material-receiving cavity and a waste-receiving bladder carried within a portion of the cavity. A flowable waste material is loaded into the bladder at a waste collection site and delivered to a treatment facility located remotely of the collection site. A portion of the material-receiving cavity of the transport vehicle is filled with a non-waste material and is transported to a drop-off site located remotely of the treatment facility. In one embodiment, the drop-off site is located relatively closely to the waste collection site. The bladder may also be collapsed into a generally flat shape for use as a tarpaulin for covering the non-waste material.

6 Claims, 8 Drawing Sheets

WASTE HANDLING METHOD

This application is a continuation-in-part of U.S. patent application Ser. No 601,873, filed Oct. 23, 1990, entitled Means and Method for Enhancing Plant Growth Under Field Conditions, now U.S. Pat. No. 5,261,9

FIELD OF THE INVENTION

The present invention relates generally to the field of waste handling, treatment and disposal. In particular, the invention provides a method for efficiently transporting, treating and utilizing a flowable waste material.

BACKGROUND OF THE INVENTION

Researchers are continually searching for new methods to treat and dispose of waste materials. Finding a cost-effective, environmentally safe method of dealing with waste has always been problematic, and the problem is particularly acute in large cities and other areas with high population densities in such areas, the value of land tends to be rather high, adding significantly to the capital costs of providing a proper waste disposal site. Operational costs associated with transporting the waste, however, may offset the capital cost savings gained by moving the waste to a remote location where land values are lower. This is particularly true in the case of waste water, primarily because the cost of building and maintaining a waste water pipeline between the city and a distant location often vastly outweighs the cost savings associated with the land itself. Accordingly, it would be desirable to provide a reliable, cost efficient method for transporting waste water from one location, such as a city, to another location, such as a rurally located treatment facility.

Waste materials, including both solid wastes and waste water, represent significant potential sources of energy. Some municipalities have attempted to recove this energy and reduce the amount of solid waste deposited in landfills by incinerating solid waste. However, such garbage incinerators are meeting increased resistance due to their high cost and the risks they impose to the environment.

As an alternative to incineration, others have used anaerobic decomposition, i.e., decomposition in a low oxygen or oxygen-free environment, as a means of treating organic waste on a small scale. The main products of anaerobic decomposition include carbon dioxide ($CO_2$), methane ($CH_4$), hydrogen sulfide ($H_2S$), and nitrogen-rich solids. As methane is a primary component of natural gas and is readily combustible, methane produced by anaerobic decomposition of waste can be burned to produce energy without posing any significant environmental hazard such as those presented by common incinerators. Furthermore, the nitrogen rich solids which are produced in this type of decomposition tend to be dispersible in water and may be used as a fertilizer or soil conditioner. Because anaerobic decomposition is an environmentally safe method for utilizing the energy stored in waste materials and because this process can provide a valuable fertilizer source, it would be desirable to have a method of utilizing this natural biochemical process on a large scale.

It has long been known that the growth rate of plants generally bears a proportional relationship to the concentration of carbon dioxide in the ambient atmosphere—a low carbon dioxide concentration tends to stunt the growth of the plant while an elevated carbon dioxide concentration can significantly increase the rate at which the plants grow. Although enhanced carbon dioxide concentration has been used in enclosed environments, such as greenhouses, utility of this technique in growing plants under field conditions is rather limited because the carbon dioxide becomes diluted by the ambient atmosphere and is blown away by the wind. Accordingly, it would he desirable to provide a means of utilizing enhanced carbon dioxide concentration to grow plants, such as trees, under field conditions.

SUMMARY OF THE INVENTION

The present invention provides a method of handling waste that is both commercially advantageous and environmentally safe. In one embodiment, the invention provides a method for economically transporting waste from one location to another, treating the waste to produce a biogas, and utilizing a portion of that biogas to enhance plant growth and/or as a fuel source.

Another embodiment of the invention comprises a method of handling waste which utilizes a waste-receiving bladder carried within a material-receiving cavity. A flowable waste material is loaded into the bladder at a waste collection or storage site and the waste material is transported to a remote treatment facility. The waste material is then removed from the bladder and delivered to the treatment facility, where it may be processed. The cavity within which the bladder rests may then be filled with a non-waste material and the non waste material is transported to a drop-off site. Thus, one may haul waste in one direction and a non-waste material in another direction, all using the same transport means, without contaminating the non waste commodity.

In another embodiment, the invention provides a method of handling waste wherein waste material is loaded into a waste-carrying vessel and transported to a remote treatment facility, where it is unloaded. The waste is then anaerobically digested at the treatment facility and a portion of the biogas resulting from the anaerobic digestion is utilized to enhance the growth of vegetation. The portion of the biogas so used is desirably relatively rich in carbon dioxide. The remaining portion of the biogas, which is desirably relatively rich in methane, and relatively carbon dioxide-poor, may then be combusted as a fuel source.

DETAILED DESCRIPTION OF THE PREFERRED EMBODIMENTS

Figure 1:
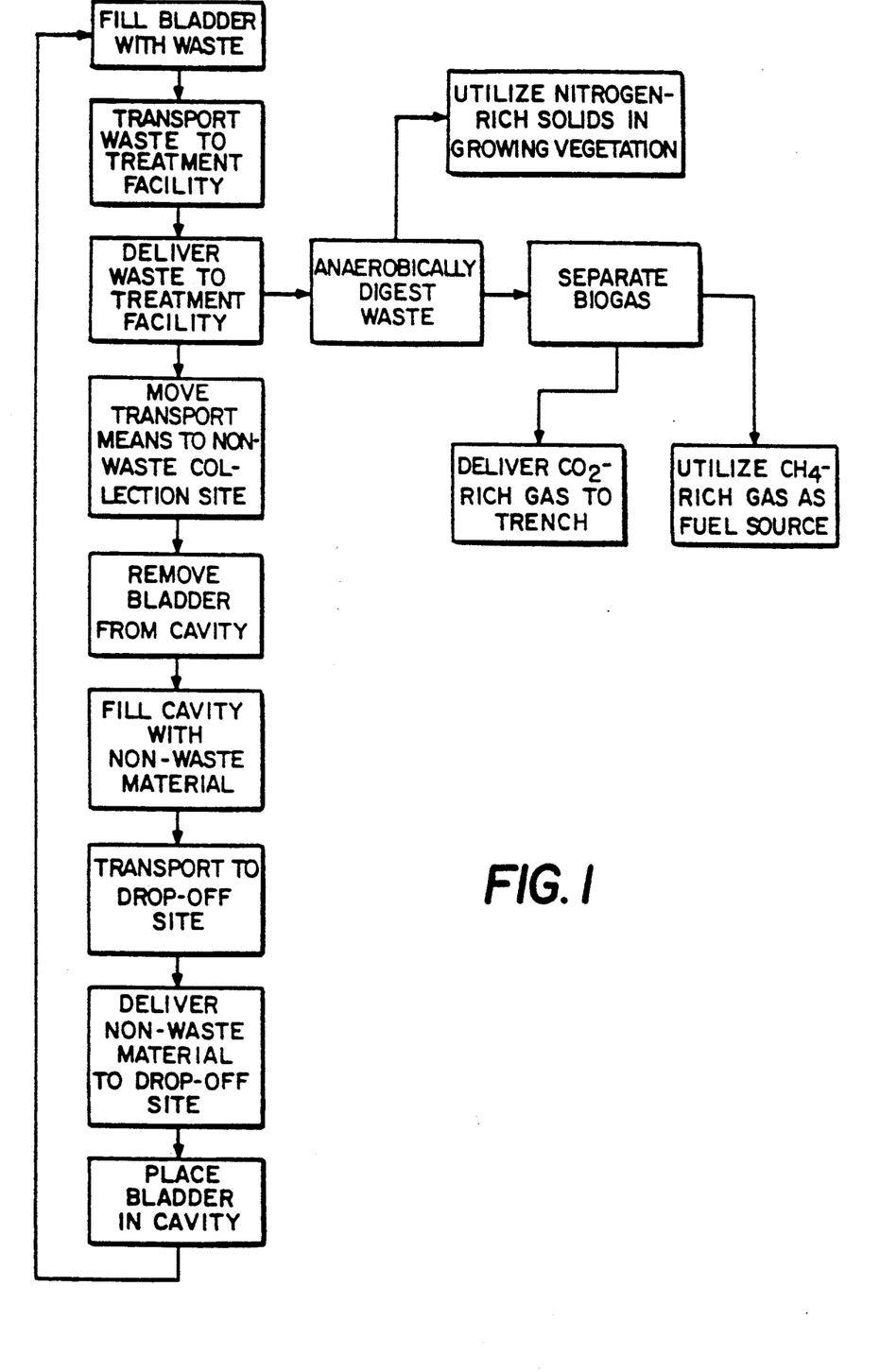
FIG. 1 is a flowchart schematically depicting the method of the invention.
Figure 2:
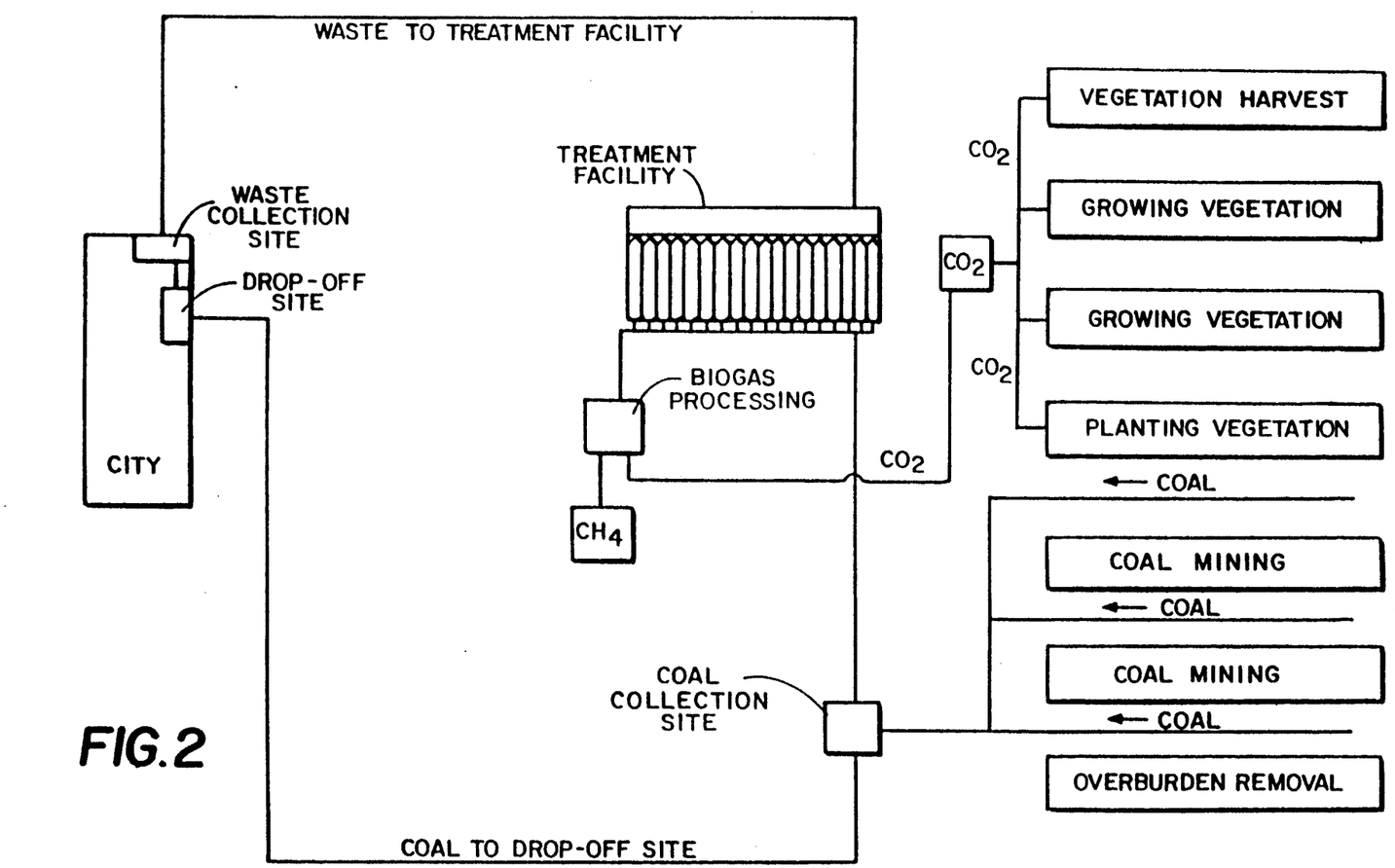
FIG. 2 is a schematic drawing showing the interrelationship of the steps of the invention.

In a first embodiment, the instant invention provides a method of economically transporting waste from one location to another. Referring to the schematic diagrams of FIGS. 1 and 2, a transport means (50 in FIG. 3) used in the invention includes a material receiving cavity (53 in FIG. 3), such as a common railroad car, and a waste-receiving bladder (11 in FIG. 3, described in detail below) carried within at least a portion of the cavity. The transport means may include any number of cavities, with a bladder being associated with each cavity. In the case of a train, the transport means could include a large number of cavities, with each car of the train defining a separate cavity.

A flowable waste material is loaded into the bladder at a waste collection site. For instance, the waste may be substantially untreated waste water from a municipality accumulated at a predetermined collection site, such as a preexisting water treatment plant. The flowable waste need not be a liquid, however; any material which is flowable may be loaded into the bladder. The waste may be a slurry of a municipal solid waste or the like, or even a flowable solid without any significant liquid content, e.g., a powdered solid such as coal ash.

The waste is desirably loaded by known means into the bladder to fill substantially the entire volume of the material-receiving cavity of the transport means. When so filled, the bladder may line substantially the entire interior of the cavity. Once the bladder is filled, the waste may be transported to a remote treatment facility. Although this facility may be fairly close to the waste collection site, in most circumstances it will be located a significant distance away from that site. If the waste collection site is in a city or other high population density location where land value is relatively high, for example, it would be economically beneficial to locate the treatment facility relatively far away from the collection site at a place where the cost of real estate is significantly less and environmental and public health risks are minimized. In a particularly preferred embodiment set forth below, wherein coal unit trains are employed as the transport means, the treatment facility may be positioned hundreds of miles from the waste collection site without unduly increasing transportation costs.

Upon reaching the treatment facility, the waste is unloaded from the bladder and delivered to a treatment facility for processing. The treatment of the waste may be carried out in any known manner, with the treatment chosen depending upon the nature of the waste. For example, in a preferred embodiment described below, organic wastes are anaerobically digested. If the waste is not capable of being broken down in this manner, it would obviously be preferable to utilize a different treatment regimen. Some waste materials may be essentially untreatable and their "treatment" may simply comprise interment in a landfill.

Due to the fact that different classes of waste may require different types of treatment, it may be desirable to segregate the waste, particularly if the transport means includes a plurality of bladders This permits one type of waste, such as a relatively high-solid slurry, to be loaded into one bladder and another type of waste, such as a relatively low-solid waste water, to be loaded into another bladder in a different cavity. When delivering waste to a treatment facility, the various types of waste could be directed to different areas of the same treatment facility or could be directed to entirely different treatment facilities, with each facility being designed to handle a different type of waste. If the latter approach is used, additional waste could be collected at a second waste collection site to refill bladders emptied at one of the treatment facilities.

When the flowable waste is delivered to the treatment facility, the bladder desirably is substantially emptied of its contents. This permits the bladder to be collapsed to a generally flat configuration, as described below The bladder may then be substantially removed from the material-receiving cavity, placing the cavity itself in condition for receiving material rather than holding the bladder. In removing the bladder from the cavity, it should be sufficiently disposed away from the opening or openings through which the cavity is commonly filled so that the cavity may be unobstructedly filled with another material.

Also after the waste in the bladder is delivered to the treatment facility, the transport means is moved to a collection site for a non-waste material. This movement may occur before or after the bladder is removed from the cavity, or the bladder could be removed while the transport means is in transit. Any type of commodity may be stored or collected at this non-waste collection site, and virtually any such site may be served according to the present invention. For instance, the site may be a warehouse for goods of the type commonly carried by the chosen transport means. In a particularly preferred embodiment set forth below, the non-waste collection site may comprise a strip mining site where a mineral, such as coal, is extracted from the ground.

Once the transport means reaches the non waste collection site and the bladder has been substantially removed from the cavity, the cavity may be filled with the non-waste material or materials held at this collection site. The non-waste material in the cavity is then transported and delivered to a drop-off site where the non-waste material is desired. As with the non-waste collection site, the nature of the drop off site served will depend upon the type of commodity being transported. For example, if the non waste material being hauled is coal, the drop off site may be a coal fired power plant. Although a single drop off site will usually suffice, at times it may be preferable that a single load of commodities carried by the transport means be delivered to a multiplicity of drop off sites, particularly if the transport means includes a plurality of material receiving cavities.

The method set forth above may be readily repeated to provide a continuous means for hauling waste material to a treatment facility in one direction and transporting a non-waste material in the other direction. If such a repetitive circuit is desired, the bladder should be replaced in its original position in the material receiving cavity and transported to the waste collection site to be refilled with flowable waste. Such a repetitive circuit is particularly useful when the drop off site is located relatively closely to the waste collection site. In this case, the transport means may be transported a relatively short distance from the drop-off site to the waste collection site, minimizing the distance traveled without any payload to cover operating costs.

As noted repeatedly above, the present invention is particularly useful in connection with a mining operation. In current coal mining practice, coal removed from a mining site, such as a strip mine, is delivered to a drop off site where the coal is used or processed. This is commonly accomplished by means of unit trains having a large number of individual, open-topped railroad cars. These unit trains run a circuit from the mining site to the drop off site and back. While the mine is commonly located in a rural area, the drop-off site is often a power generating facility, such as a coal-fired power plant, located close to a distant city or municipality which consumes the generated power. Once a train has delivered a load of coal, it usually "deadheads" back to the mine site; that is, they make the return trip without any payload. Such deadheading is economically unattractive in that it obviously does not generate any income to cover the cost of transporting the empty train.

According to the method of the present invention, such deadheading can be substantially eliminated. Drop off sites for coal are commonly located in high population density areas which tend to generate a large amount of waste. Since the drop-off site and the waste collection site may readily be located relatively closely to one another as noted above, this holds deadheading down to a minimum because a payload of waste may be loaded into a bladder on the transport means shortly after a non waste material is delivered at a drop off site. At the opposite end of the circuit, the treatment facility may be located very near the mining site. Mines are commonly located in areas where the value of the land itself is relatively low, particularly once the minerals have been extracted from the land. Desirably, the treatment site is located at the mining site and, in a particularly preferred embodiment set forth below, the treatment facility may be incorporated into a strip mining site and is useful in helping to reclaim the strip mine land. Although unit trains are often required to operate on a fairly tight schedule in order to meet the coal requirements of some power generating facilities, if waste is collect from only a single site and delivered to a single treatment facility, a significant commercial advantage can be gained by carrying a payload on the otherwise empty return trip without significantly delaying the train's schedule.

Figure 3:
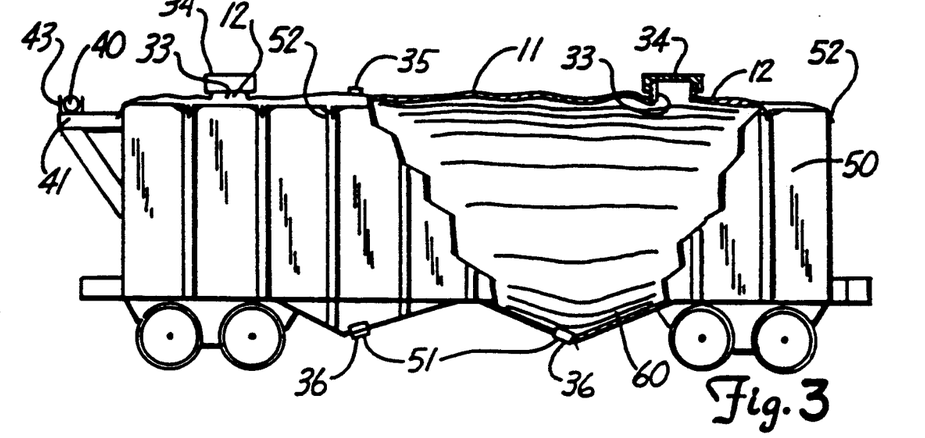
FIG. 3 is a side view of a transport means within which is carried a bladder useful in the present invention.
Figure 4:
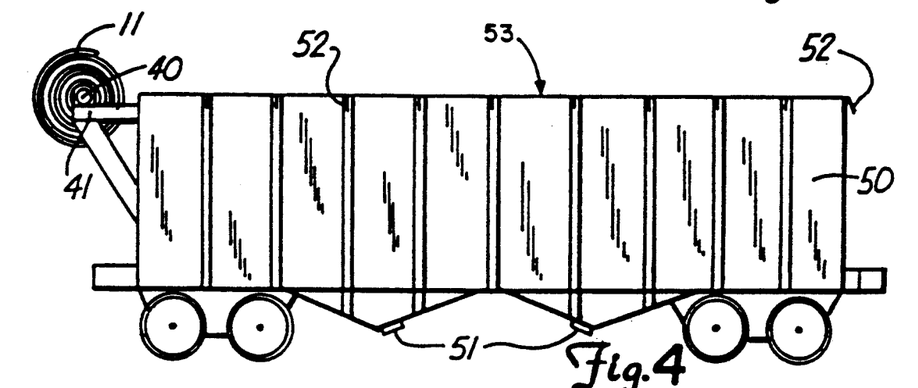
FIG. 4 is a side view of the transport means of FIG. 3 showing the bladder in a collapsed, rolled configuration.
Figure 5:
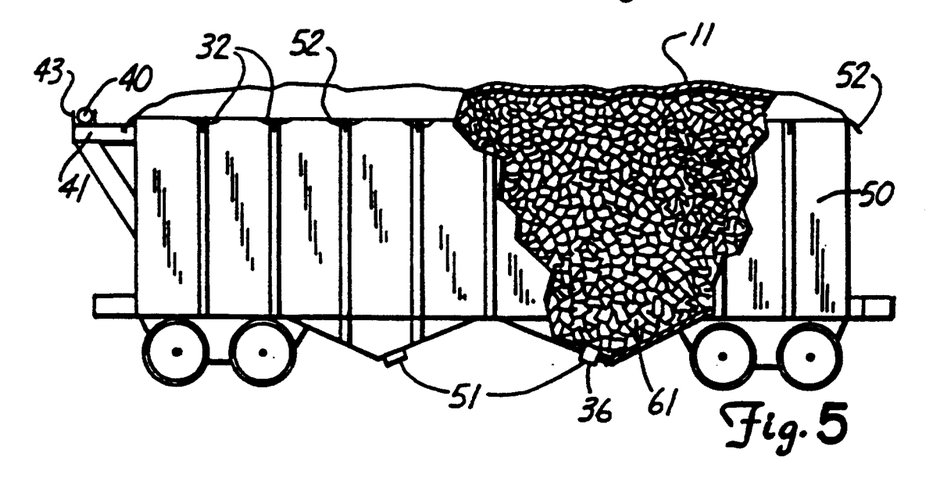
FIG. 5 is a side view of the transport means of FIGS. 3 and 4 showing the bladder deployed as a tarpaulin to cover non-waste material carried by the transport means.

One preferred embodiment of a bladder for use in the present invention is shown in FIGS. 3-5 and described in the current inventor's U.S. Pat. No. 4,909,156 (the teachings of which are incorporated herein by reference). The transport means depicted in these figures comprises an open-topped railroad car, such as those commonly used for hauling coal. The 3-dimensional generally rectangular flexible bladder 11 is placed within the material receiving cavity 53 defined by the bottom and walls of the railroad car 50. This enables a flowable material 60 to be carried within the railroad car, as noted above. Desirably, the bladder is formed out of a strong, durable rubber material with adequate flexibility to allow it to conform to the interior of the railroad car 50. The bladder 11 is structurally supported by the railroad car 50 and preferably comprises the fully enclosed, substantially leak-proof bag suitable for transporting flowable waste. The material of which the bladder is made should possess good chemical resistance properties so that its performance is not substantially affected by the waste carried within it or the environment to which it is exposed.

Carried by the upper portion of the bladder 11 are one or more closable filling ports 12 through which flowable waste may be introduced to the bladder. Preferably, the filling ports 12 comprise rigid threaded hose fittings 33 which are permanently attached to the upper portion of the bladder and contain a central opening through which the flowable waste may be added to the bladder. A threaded cap 34 may be screwed onto the hose fitting 33, providing a seal to keep the waste in the bladder. A locking device may be included on the filling ports to prevent unauthorized persons from gaining access to the inside of the bladder. A gas release valve 35 may be included to allow gases to escape when the bladder is being filled. The gas release valve 35 may also employ automatic pressure relief means for releasing accumulated gas from the bag as necessary, e.g., gas pressure accumulated under elevated temperature conditions.

Carried by the lower portion of the bladder 11 are a plurality of emptying ports through which the waste may be emptied for delivery to the treatment facility. The emptying ports may comprise a plurality of closable discharge ports 36 which may be adjustable so that the flow rate of the waste exiting the bladder 11 ma be controlled. The discharge valves 36 may protrude into the proximity of the hopper doors 51 of the railroad car 50 so that the valves can be easily opened when the hopper doors are opened. The flow of waste through the discharge valves may be induced by gravity, or may be facilitated by pressurization. The discharge valves 36 may be of an obstruction screw type which would allow the valves to be adjusted to the desired flow rate. The discharge valves may include a suspension rope so that they may be removed from the hopper doors 51 from a remote position.

When the bladders 11 are not being used to transport waste, they may be collapsed into a generally flat shape, as noted above. If the material receiving cavity 53 of the transport means is open topped, as shown, the bladder may be used as a tarpaulin to cover non-waste material 61 carried by the railroad car 50. The bladder thus serves to provide a waterproof cover to protect the cargo 61 from the elements and to prevent the cargo from spilling or blowing out of the car during transport (e g., coal dust).

The bladder 11 may be provided with attachment mean through which an anchoring line 32 may be passed for removable attachment to the railroad car 50. The anchoring line 32 is preferably secured to the railroad car by threading the anchoring line through anchoring means 52 carried by the railroad car. A pair of end lashing ropes may be used to secure the ends of the collapsed belabor to the respective ends of the railroad car and to stretch it across the non-waste material carried by the railroad car.

Any suitable means may be used to substantially remove the emptied bladder from the material-receiving cavity 53. In the embodiment shown in FIGS. 3-5, a movable rolling bar 40 and retaining means 41 for the rolling bar is provided to remove the bladder from the cavity. The emptied bladder 11 is removed from the railroad car by attaching one end of the bladder to the rolling bar 40 and rolling this rolling bar closely along the top surface of the bladder, accumulating the bladder thereupon in a spiral roll configuration as exemplified in FIG. 2. This spiral roll may then be placed on the rolling bar retaining means 41 which is carried adjacent an end of the railroad car, with the opposing ends of the rolling bar being securely retained by the retaining means 41. Alternatively, the bladders may be collapsed into their generally flat configuration and stacked on top of one another on a separate railroad car, such as a flatbed car, dedicated for this purpose.

In order to fill the bladder with the flowable waste material, the bladder is placed inside the material-receiving cavity of the railroad car 50 with its discharge valves 36 closed. The valves are placed adjacent the closed hopper doors 51 of the railroad car carried by the discharge valves 36. Once the valves are in place, the bladder 11 may be lowered into the car and positioned so that&it generally evenly covers the floor of the car throughout its length. In order to minimize wear on the bladder, a padding material, such as a durable blanket, may be placed within the material-receiving cavity between the bladder and the points in the railroad car causing the most wear on the bag. Obviously, the blanket should be provided with a hole or the like adjacent the discharge valve 36 so that it does not hamper the discharge of the waste.

The caps 34 carried by the filling ports 12 are opened and a filling hose may be applied to the filling port. The flowable waste may then be loaded into the bladder by means of a pump, an auger, or other suitable means. The bladder should be reasonably monitored during this loading process to ensure that it is properly and evenly seated in the car before the bladder becomes too heavy to adjust. As the bladder is filled with the flowable waste, it conforms to the shape of the material-receiving cavity When the bladder is filled to a predetermined level, preferably adjacent but below the top rim of the car, the flow of waste is stopped, the filling hose is removed, and the caps 34 are replaced. When unloading the waste from the bladder for delivery to the treatment facility, the hopper doors 51 are positioned over a suitable discharge point and then opened to expose the bladder's discharge valves 36. The discharge valves may then be opened sufficiently to achieve the desired flow rate. When the bladder is empty, the discharge valves are closed and the bladder is ready to be collapsed and removed from the material-receiving cavity, such as by utilizing the rolling bar described above.

Bladders of this type may be used for a relatively large variety of railroad cars; preferably the bladders are tailored to fit the particular car configuration in which they are used. In the case of a rotary dump car, the car may be rotated and the bladder drained through the fill port 12. Obviously, this would necessitate providing means for holding the bladder in the railroad car as it is upturned. Alternatively, the bladder contents may be siphoned out through the fill port, or the bladder may be pressurized at one port to expel the contents at another port, or the bladder may be compressed to expel the contents through one or more ports. If a higher flow rate were desired, more discharge valves 36 could be used, or a significantly larger opening could be provided, which opening may be elogate with a length approximately equal to the width of the hopper doors 51.

In a second embodiment, the present invention includes the steps of anaerobically digesting the waste at the treatment facility an utilizing by-products of this anaerobic digestion as a fuel source and to enhance the growth rate of plants.

As explained above, anaerobic decomposition is a natural biochemical process which occurs when organic materials decay in an environment with a limited oxygen content. The products of such a decomposition include $CO_2$, $CH_4$, and nitrogen rich solids. A system for anaerobically digesting waste is set forth in U.S. Pat. No. 4,897,195, which is also owned by the current inventor The teachings and disclosure of that patent are incorporated herein by reference. This digester may handle a wide range of wastes, including manures, refuse, human effluent, distillery by-products, vegetable processing by-products, and other waste materials which anaerobically decompose.

A preferred anaerobic digestion system such as that set forth in U.S. Pat. No. 4,897,195 is illustrated schematically in FIGS. 6–11. The system includes a plurality of digester modules 110, which generally take the form of a somewhat flexible bag, lying on an inclined surface 118 enabling the modules to be rolled slowly, thus agitating the contents of the modules and facilitating the anaerobic digestion process. The digester modules 110 are filled with a suitable waste toward the upper-most end of the inclined surface 118 and allowed to slowly roll down this surface adjacent other digester modules 110 over a period of time sufficient to complete the decomposition process, known as the digester life cycle. The digestion process takes place within the digester modules and biogas, i.e., the gas produced in the digestion, may be removed from the digester modules while the digestion process is taking place as desired. Materials may also be added to the modules to promote the digestion process without interrupting the process.

Figure 6:
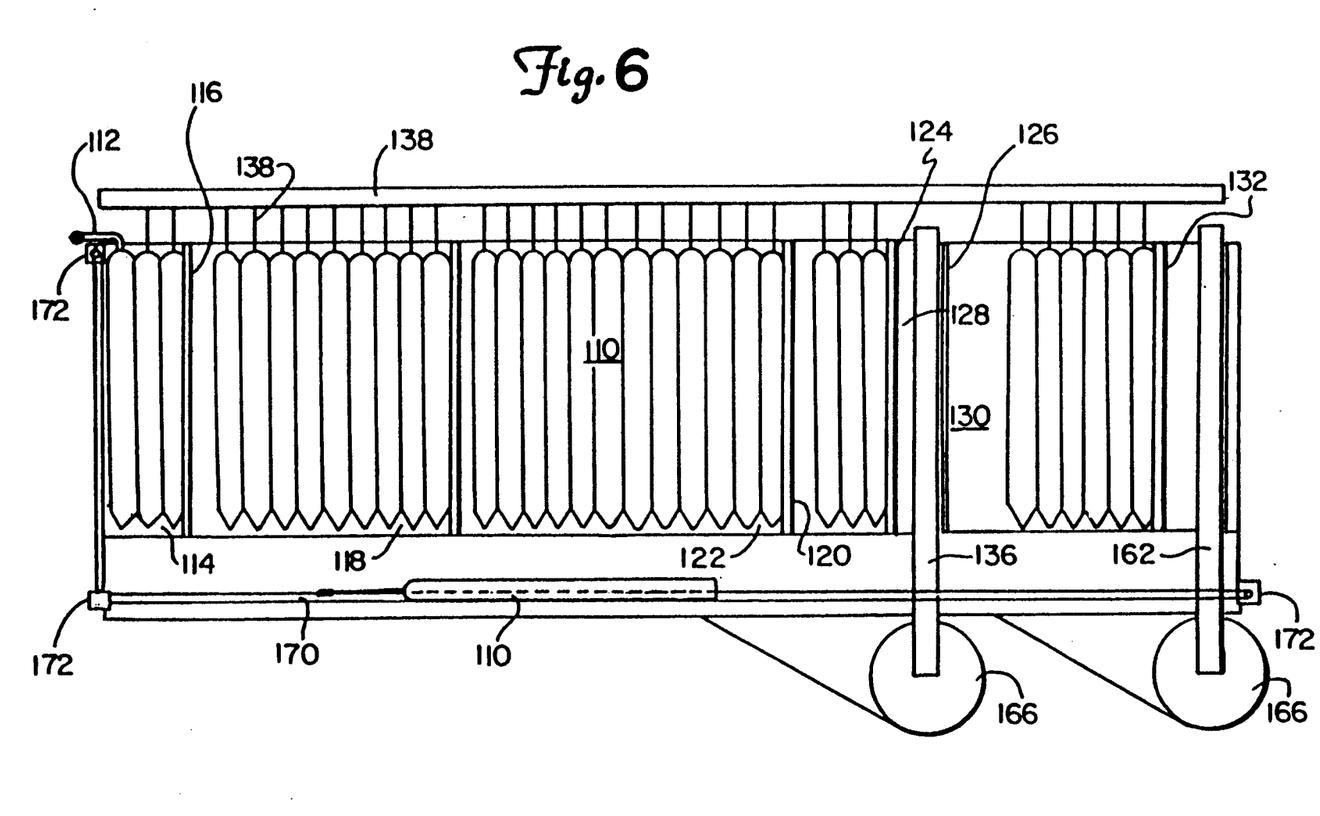
FIG. 6 is a top, somewhat schematic view of an anaerobic digestion system and process useful in the invention.
Figure 7:
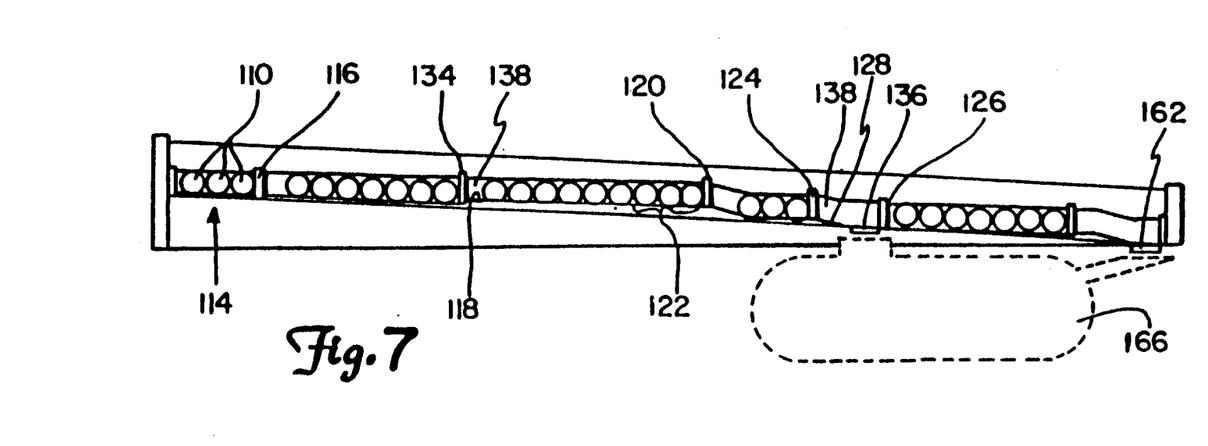
FIG. 7 is a side, elevational view of the anaerobic digestion system depicted in FIG. 6.

The anaerobic digestion system may include a heating unit (not shown) for heating the contents of the digestion modules 110 to a temperature preferably between 100° F. and 140° F. to hasten the anaerobic decomposition process. The heating means may be contained within the digestion modules or may be external to the digestion modules. In one preferred embodiment, the modules 110 are housed in a solarium type structure, described below, taking advantage of passive solar energy. This digestion system may also include testing means comprising a master gas control unit 138 for sampling the contents of the digestion modules to determine the extent of completion of the digestion process taking place within the modules and for determining what materials, if any, to add to promote the decomposition process.

Figure 8:
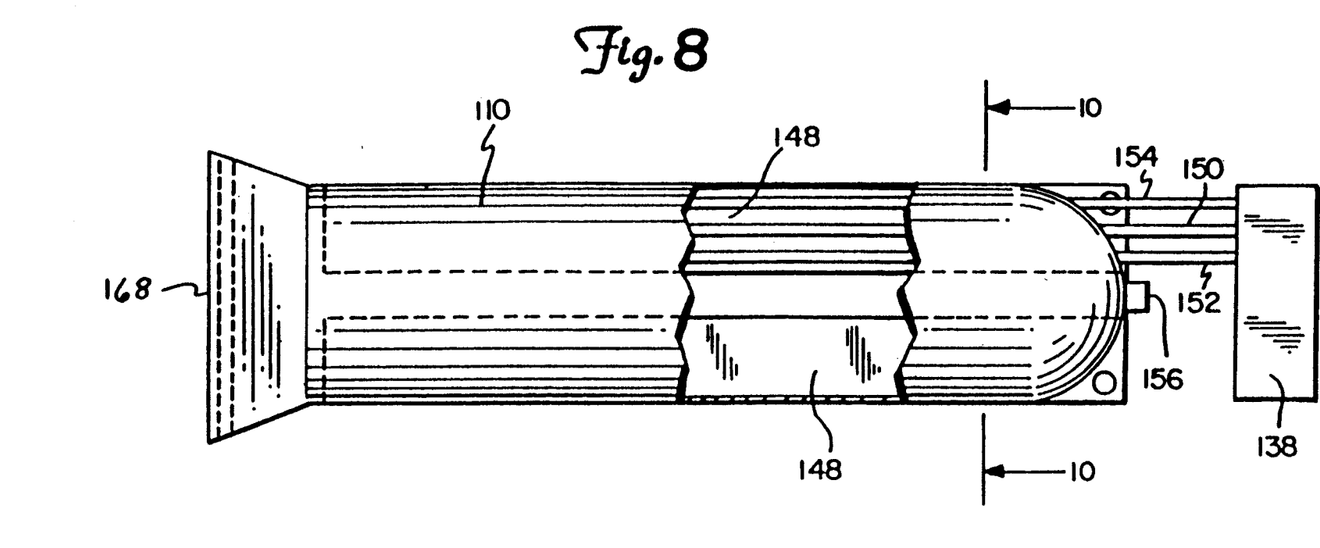
FIG. 8 is a side, partially broken away view of a digester bag of the invention.

In a preferred embodiment, the digestion modules 110 comprise generally cigar shaped synthetic bags which are liquid-tight and provide an anaerobic environment (i.e., a low-oxygen environment) in which materials can be digested. The materials from which the bags are constructed should be generally non-reactive so as not to interact with the digesting waste. As shown in FIG. 8, bags preferably include a plurality of fluid transfer ports allowing entry and exit of materials, including the organic material port 156, biogas port/line 154, sampling line 150, and doping line 52 for introduction of other substances to facilitate the digestion process.

The digestion bags are desirably generally circular in transverse cross section, enabling them to easily roll down an inclined surface. The bags may also include hardware on their external side for lifting and moving them. They may also be provided with internal agitation means for stirring and agitating the contents of the bag to promote the decomposition process and to move substances contained within the bag to a favorable location to be easily removed from the bag. This agitation means may comprise a plurality of agitator paddles 148, shown in FIGS. 8 and 10, contained within the digester bag 110 for agitating the contents of the bag as they roll down the incline 118. In a preferred embodiment, the sampling doping and gas lines (150, 152, and 154, respectively) may be suitably attached to an agitator paddle to facilitate in adding and extracting materials to and from selected portions of the module.

Figure 9:
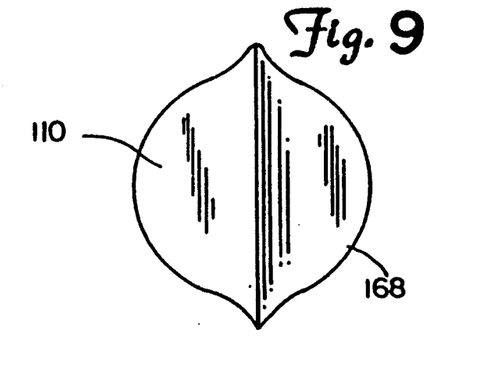
FIG. 9 is a view of the left end of the bag of FIG. 8.
Figure 10:
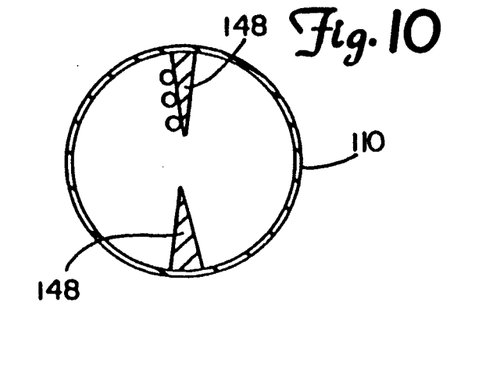
FIG. 10 is a cross sectional view of the bag of FIG. 8 taken along line 10—10 thereof.
Figure 11:
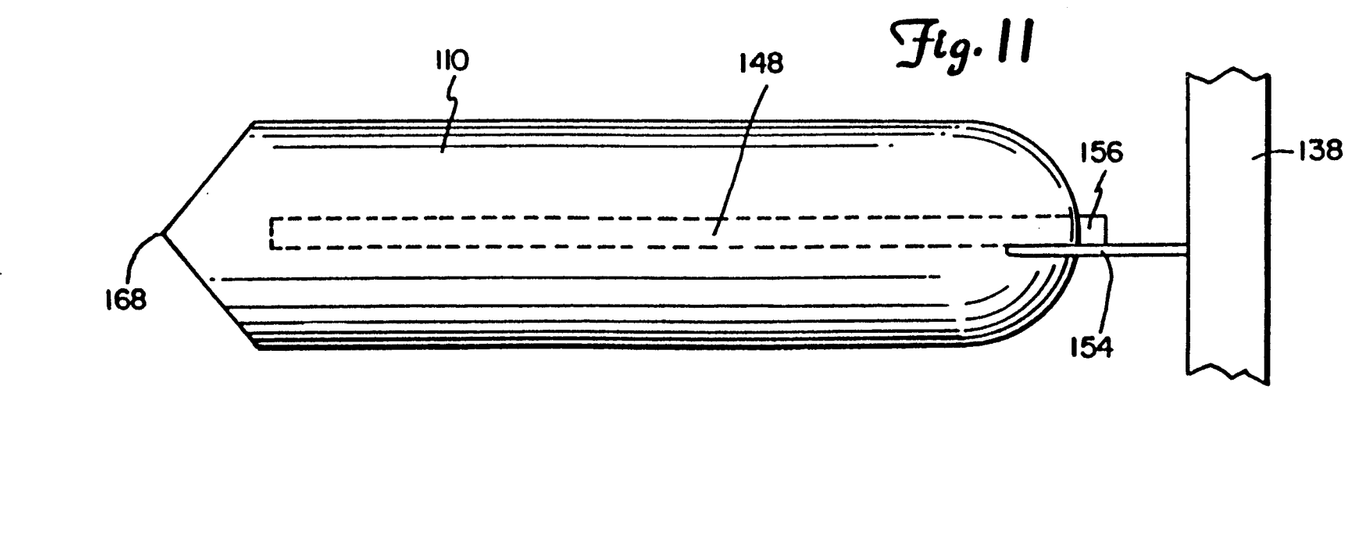
FIG. 11 is a top view of the bag of FIG. 8.

The emptying means on the digester modules 110 may comprise a closable opening for draining the contents as by pumping or alternatively may include a generally larger opening, such as that shown as 168 in FIGS. 8 and 9, enabling the contents to be dumped and may be of any suitable closable type.

In treating the waste in this anaerobic digestion system the digester modules 110 are placed in an area adjacent the highest point of the inclined planar floor. The upper-most portion of this floor is referred to as the digester head 114. The digester modules are arranged on the digester head as shown in FIGS. 6 and 7 where they are filled with the waste material. Although the digester modules 110 may be nearly filled with waste, some volume should be left for expansion as gases are produced in the anaerobic decomposition process. Living anaerobic bacteria may then be added to the waste within the module along with carbon dioxide gas and lignite to begin the digestion process.

Preferably, more than one digester module 110 is prepared in this manner on the digester head 114 before being released by the head gate 116. The head gate 116 is a movable barrier between the digester head and the inclined planar surface 118 for retaining the digester modules on the digester head until they are ready to be released. When the head gate 116 is moved out of the way of the digester modules 110, the modules are allowed to roll onto the inclined surface 118.

The digester modules 110 are allowed to roll slowly in close contact with one another along the inclined surface with their axes aligned generally parallel to one another. The material transfer lines and sampling lines 150, 152, and 154 attached to the digestion modules are preferably in free rotating engagement with the master gas control unit 138 and remain connected to the digestion modules throughout their entire journey down the inclined plane 118. The master gas control unit extends along the length of the inclined plane to continuously monitor the progress of the decomposition process. The contents of the digestion modules 110 may be sampled by the computer-controlled master gas control unit, which may automatically dope the contents of the modules as desired for the most efficient anaerobic decomposition.

The angle of the inclined plane 118 may vary from one system to the next as necessary. In most systems, the angle would be between about 0.1° and 5°, desirably between about 0.2° and 3°, and most preferably about 1°. The determinative factor is that the angle be steep enough to enable the digestion modules 110 to roll slowly down the inclined plane 118 while in close contact with other modules, but flat enough to prevent the modules from attaining excessive momentum. A number of positioning gates 134 may be included along the inclined plane for retarding movement of the digestion modules 110.

The lower end of the inclined plane comprises a digester tail 122 preferably sized to hold three digestion modules 110 carried by the inclined plane 118. A tailgate 120 is positioned at the end of the digester tail to limit movement of the modules down the inclined plane. The tailgate 120 is movable to allow one or more digestion modules 110 at a time to roll off the digester tail 122 down an accelerator ramp 128 and onto either a conveyor for removal or onto an extended cycle incline 130, depending on the extent of completion of the decomposition process. The majority of the digestion modules reaching the end of the inclined plane will desirably have completed the anaerobic digestion process and will be ready to have their contents emptied.

In order to empty the modules, a separating gate 124 is moved to allow the digestion modules that have passed by the tailgate to roll down the acceleration ramp 128 and onto a conveyor belt 136 where they are restrained from moving any further by an extended cycle head gate 126. The modules may be emptied by pumping the contents out through an opening or by forcibly dumping them into a receptacle, such as the tank 166 shown in FIG. 7. Once emptied, the digestion modules are returned to the digester head 114 where they may be refilled and reused.

The transporting means used to move the modules may, in a preferred embodiment, comprise a motorized cable system 160, as shown in FIGS. 6 and 7, for pulling modules 110 along a smooth surface. The conveying system includes a plurality of support towers 172 between which extends a continuous cable 170 to which the modules may be attached.

When a digester module 110 reaches the separating gate 124 containing waste which has not been fully digested, the separating gate 124 is opened, but the extended cycle head gate 126 remains retracted. This permits the module to enter an extended cycle incline 130 similar to the incline 118, where the module remains until the anaerobic digestion process is completed. A tailgate 132 is included with the extended cycle incline 130 to retain the digester modules 110 on the extended cycle incline 130 while the contents are still being processed. When the digestion process has been completed, the tailgate 132 is retracted to allow the digester modules 110 to pass by and proceed down an acceleration ramp 164 to a second conveyor belt 162 for removal.

In an alternative embodiment, the modules 110 are floated in a pond or other body of controlled temperature water. Rotation of the modules 110 to agitate the contents may then be accomplished mechanically, either manually at desired intervals or automatically by suitable mechanical linkages to a drive motor (not shown). Alternately, an incline 4 may be used in conjunction with such a pool. In either alternative embodiment, filling and emptying of the modules can be carried out substantially the same as with the inclined embodiment described above.

In the preferred embodiment described above wherein the treatment facility is located adjacent a strip mining location, one of the elongate trenches formed during the strip mining process may be utilized for this anaerobic digestion process. The floor of such a trench may function as the inclined plane 118. Alternatively, such a trench may be fortified, such as by techniques well known in forming earthen dams or by lining the trench with a layer of concrete or a large rubber liner.

This trench ma then be flooded with water within which the modules 110 may be floated, as noted above. An insulating dome would be placed over the strip to maintain the elevated temperature necessary for anaerobic digestion.

As noted above, the biogas produced during this anaerobic decomposition process may be extracted through the biogas port/line 154 in the digestion module 110 The biogas extracted from each such module may be carried through the master gas control unit 138 to a central collection site. Once the biogas has been collected, it may be utilized as desired, such as by simply combusting this gas to produce heat, which heat may in turn be used to maintain the contents of the digestion modules at an elevated temperature. In the alternative embodiments employing a body of controlled temperature water, this energy produced may be used to heat the water and thereby maintain the digester modules at the elevated temperature.

In a preferred embodiment, however, the biogas is separated into a relatively carbon dioxide rich gas and a relatively carbon dioxide poor gas. It is preferred that the carbon dioxide-rich gas have only a minimal methane content to minimize the flamability of this gas. The carbon dioxide-poor gas, therefore, has a higher methane content and is more inflamable, making it a more efficient fuel source. The separation of the biogas into its various components may be accomplished by any of a wide variety of means well known in the art.

The biogas produced by the anaerobic decomposition may be utilized in any desire manner. However, in a preferred embodiment, a portion of the biogas is used to enhance the growth rate of plants. As noted above, the growth rate of the vegetation may be significantly increased by enhancing the concentration of carbon dioxide adjacent the plants. The present invention therefore utilizes a portion of the biogas—preferably a carbon dioxide-rich portion—produced at the treatment facility to augment the growth rate of vegetation.

This may be done by any known means. The carbon dioxide-rich gas may simply be supplied to an enclosed greenhouse environment. This will obviously increase the carbon dioxide concentration of the ambient air within this enclosure, thereby increasing the growth rate of the plants.

Figure 12:
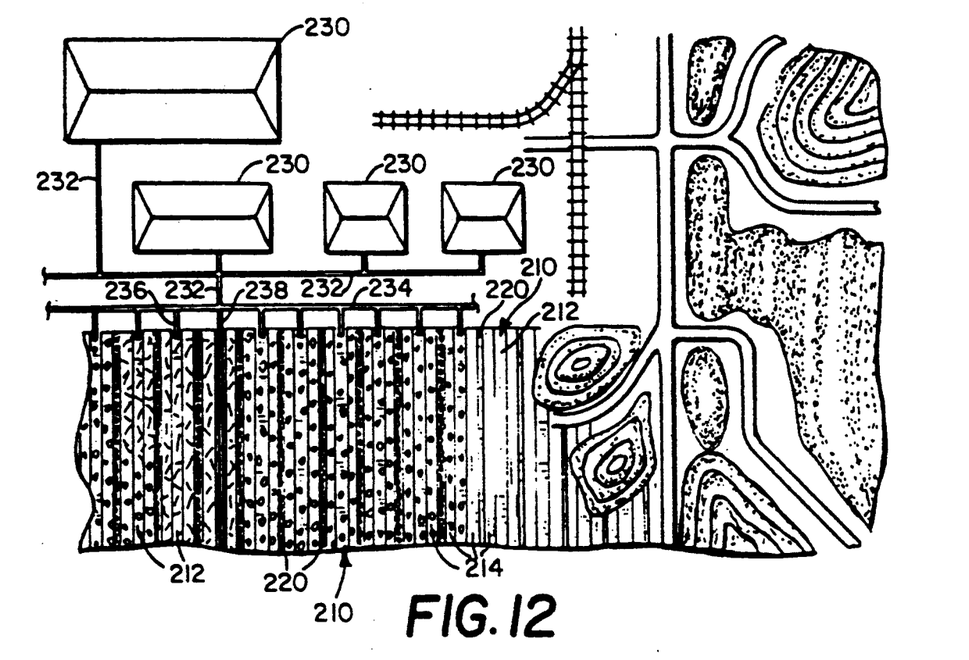
FIG. 12 is an aerial view of a plant growing system according to the present invention.
Figure 13:
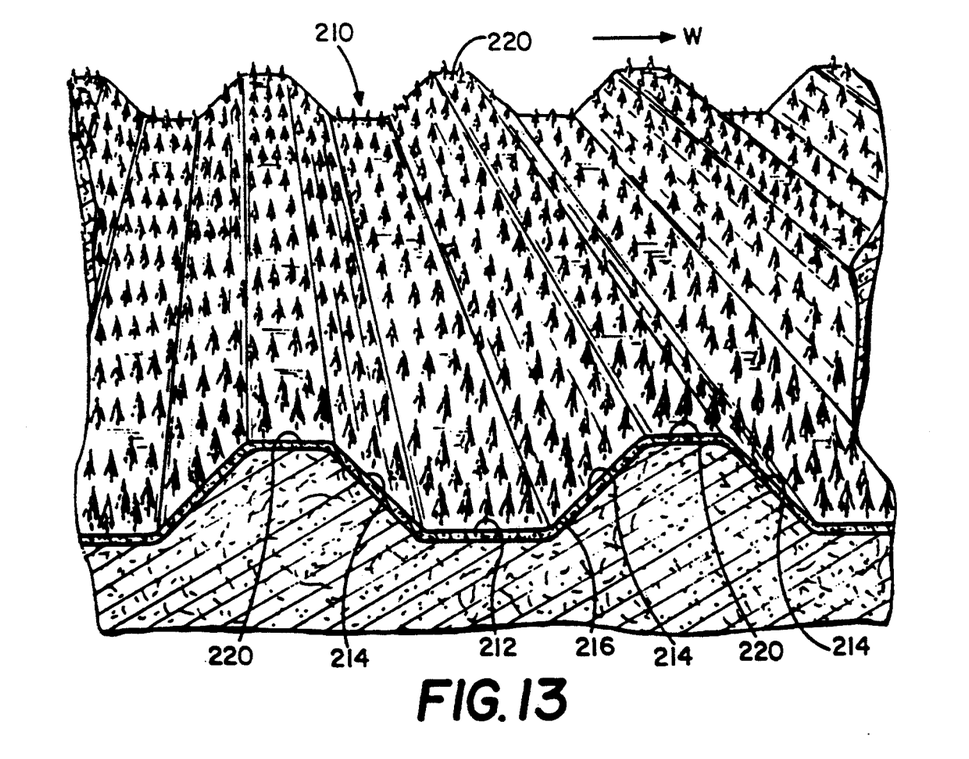
FIG. 13 is a partially cut away, perspective view of the invention of FIG. 12.
Figure 14:
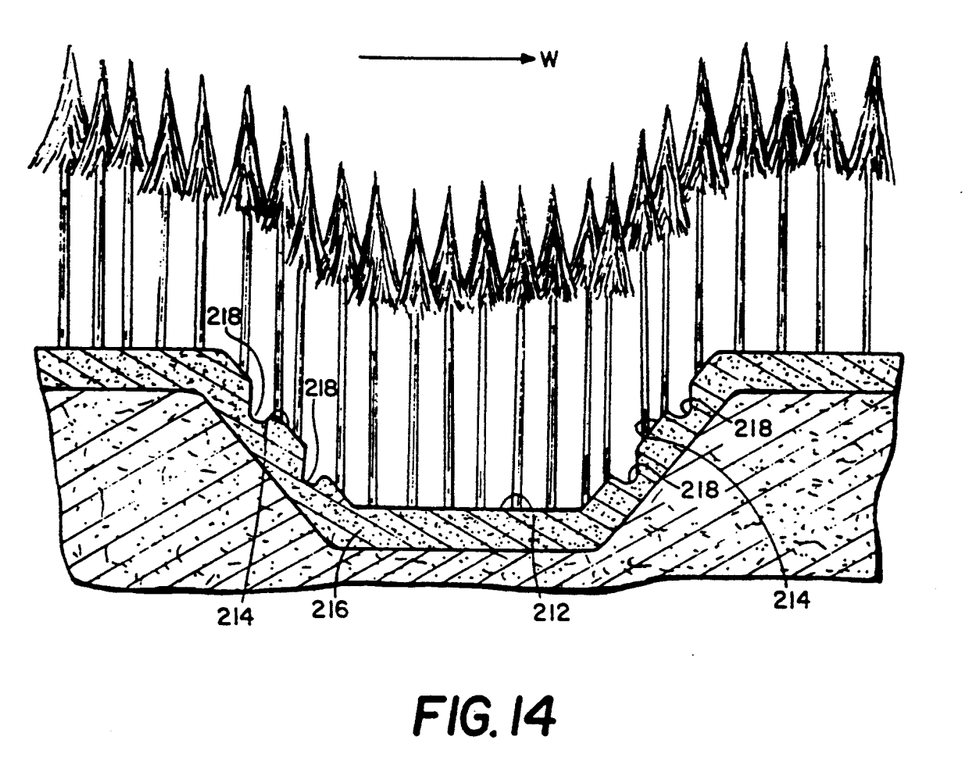
FIG. 14 is a cross-sectional side view of a trench of FIG. 12.

In a particularly preferred embodiment, however, the carbon dioxide-rich gas is supplied to plants growing under field conditions. Such a system is depicted in FIGS. 12-14. This system is described in detail in the present inventor's copending U.S. patent application Ser. No. 601,873, filed Oct. 23, 1990, the teachings of which are incorporated herein by reference A system for enhancing plant growth according to the present invention is shown in FIGS. 12-14. The system includes at least one elongate trench 10 in which a plurality of plants may be grown. The trench comprises a floor 212 and a pair of sidewalls 214 which extend along the length of the trench. The sidewalls desirably slope generally outwardly and away from one another in an upward direction. The sidewalls 214 of the trench 210 are designed to minimize loss of carbon dioxide from the environment of the trench; if the sidewalls are too short or the slope is too gradual, their ability to retain carbon dioxide within the trench will suffer. If the sidewalls 214 are too steep, however, the effects of erosion will be more pronounced, adversely affecting their long-term stability. Although erosion can be checked by known means, such as employing a ground cover of smaller vegetation with extensive root systems, the slope of the sidewalls must be optimized by balancing these two competing considerations. Other factors, such as the nature of the soil and average rain fall at the site, must also be taken into consideration. Accordingly, the slope of the sidewalls 214 will tend to be relatively site specific.

If so desired, a layer of top soil 216 may be enriched with fertilizers, such as a nitrogen-rich fertilizer, or other known chemicals which are useful in enhancing the growth of vegetation or increasing its resistance to disease or parasites. The nitrogen-rich solids which result from the anaerobic digestion process in the treatment facility described above may be used as a fertilizer.

Elongate ditches 218 may also be provided in the sidewall. These ditches may, for example, be used for irrigation or, as explained below, elongate conduits for delivering carbon dioxide to the trench may be placed within these ditches. Although a pair of trenches are shown spaced from the floor 212 and one another on each sidewall 214, the number and location of ditches may be varied a desired.

In a preferred embodiment, a plurality of such trenches 210 are provided, with the trenches being oriented generally parallel to one another. A sidewall 214 of each trench is positioned adjacent the sidewall 214 of another trench, with the adjacent sidewalls defining a ridge 220. Although the sidewalls may directly abut one another to define a narrow ridge at the apex of the sidewalls, the ridge is desirably somewhat wider and may be substantially horizontal, as shown. Such horizontal ridges not only help minimize erosion, but they also provide a suitable planting surface for additional vegetation which may act as a windbreak, serving to further reduce the wind currents. The plants grown on the ridge to create the windbreak may all be of the same variety, and at approximately the same stage of growth, but this is not preferred. Instead, it is desirable to provide a windbreak composed of both tall, mature plants, such as mature trees, and a variety of shorter plant life to more effectively shelter the trench from wind turbulence For reasons explained below in connection with the delivery of carbon dioxide to the trench, it may be desirable to provide a sloped floor 212. In a preferred embodiment, the floor slopes downwardly from one end of the trench toward the other at a gradient of between about 0% and about 10%. A gradient of about 10% was found to work well in a laboratory test.

The trenches may be oriented as desired. Although the layout of the land may effectively dictate the direction of the trenches, they are preferably oriented generally perpendicularly to the "prevailing wind direction." Obviously, the precise direction of wind currents adjacent the trench will vary over time. However, the historic weather patterns of many areas indicate that weather systems, and hence wind, will more frequently tend to move in a certain general direction. This direction is referred to herein as the "prevailing" wind direction, and is indicated in FIGS. 13 and 14 by the arrow designated "W."

Orienting the trenches such that they extend generally perpendicularly to this prevailing wind direction improves retention of carbon dioxide within the trench. If the wind travels in a direction substantially parallel to a trench, it will carry carbon dioxide rich air within the trench along the length of the trench and out one end thereof. As the wind direction approaches from a direction substantially perpendicular to the length of the trench, though, the sidewalls 214 and the windbreak, if any, on the ridges 220 impede the flow of air into the trench. By so restricting the passage of air into and through the trench, the sidewalls and the ridges serve to prevent the carbon dioxide rich air which is supplied to the trench from being either diluted by or carried off with the ambient air.

FIGS. 12-14 depict the trenches of the present system as being substantially straight along their length. While the depicted construction is preferred, the invention may be practiced in trenches which may significantly deviate from a straight path.

The invention is particularly well suited for use in reforestation of denuded tracks of land. As noted above, in a preferred embodiment, the present invention is used in conjunction with a strip-mining operation. In the process of strip-mining of minerals, such as coal, the soil above the mineral deposit is systematically pushed aside to provide access to the deposit. In so doing, large, elongate mounds of the cleared earth are commonly formed. Those carrying out such mining are required by law (see, e.g., 30 U.S.C. §1201 et. seq.) to reclaim the land, i e., to repopulate the site with vegetation, after the mining is completed. The current standard practice in the industry is to redistribute these elongate mounds to more or less recreate the original contour of the land and then plant vegetation on this new landscape.

Strip-mining sites may instead be modified according to the instant invention. An elongate mound of cleared earth produced in the mining process may be formed to define a ridge 220 and the adjacent sidewalls 214 of two trenches of the invention. When two or more such ridges are so formed, suitable trenches may be defined. In the short term, this would be beneficial in that the cleared earth would not have to be as extensively redistributed from the series of long mounds. In the long term, this would transform the former site of a mine from a commercially unproductive eyesore into a productive tract of land. In particular, the land may be planted with trees which can be sold as timber or as a raw material for forming pulp or combustible fuels, rather than merely lying fallow.

As noted above, a trench of the invention is provided with a supply of carbon dioxide rich gas to accelerate growth of the plants in the trench. Although it may vary slightly, the average concentration of carbon dioxide in the ambient atmosphere is on the order of 0.03%, or 300 ppm. It is an object of the present invention to augment this concentration within the trench to at least about 0.06-0.20% (1500-2000 ppm). Although this concentration may be increased significantly more than that, if carbon dioxide comprises 10% (100,000 ppm.) of the ambient air, this may be toxic to animals which may live in the trench and workers who tend the trench. Furthermore, the beneficial effects of the heightened carbon dioxide concentration on plant growth are believed to diminish at concentrations of about 5% or more. Hence, it is preferred that the carbon dioxide concentration in the air within the trench be maintained at a level between about 0.06% to about 5%, with a range of about 0.06% to about 2% being preferred.

It is well known that at standard temperature and pressure, carbon dioxide gas is denser than atmospheric air. In particular, the density of carbon dioxide gas is approximately 1.5 times that of an average ambient air composition. Accordingly, if one were to release a carbon dioxide-rich gas into the trench adjacent the floor 212, this denser gas would tend to stay within the trench absent any disturbance by air currents. Thus, the sidewalls 214 and the vegetation, if any, planted on the ridge 220, serves an important function—by limiting wind turbulence in the trench, the loss of carbon dioxide from the trench is minimized. Under high-velocity wind conditions, though, these measures alone may prove to be insufficient to contain the carbon dioxide in a trench for an extended period of time. This is particularly true when vegetation in the trench is dispersed because the plants which are being treated with the carbon dioxide-rich gas will not actively prevent the loss of carbon dioxide.

In a preferred embodiment, the plants grown in a trench of the invention are "overstocked," i.e., they are planted more closely together than their optimum spacing under normal conditions. This will encourage the formation of a "closed canopy" as the upper portions of the plants grow rather close together. In the case of trees, for example, the upper branches of adjacent trees may tend to become interlaced with one another if the trees are planted too closely together. Such a closed canopy tends to result in the depletion of carbon dioxide from the air beneath the canopy because the supply of replenishing air is restricted by the presence of this closed canopy. While the leaves on a plant which are positioned above the "canopy" are exposed to the circulating ambient air, leaves below the canopy scavenge carbon dioxide from the air underneath the canopy. The level of carbon dioxide beneath the canopy is therefore reduced quite rapidly. Whereas the closed canopy restricts the flow of fresh air supplies to the underside of the canopy, this same restriction of gas flow through the canopy will trap the carbon dioxide-rich gas in the trench.

Although a wide variety of plants may be grown in a trench of the invention, trees which grow well under overstocked conditions are generally preferred. Such trees include, for example, salixaceae populas tremuloides (quaking aspen). Alternatively, sorghum, a grain, may be used instead, as it has shown an ability to grow well when heavily stocked.

Carbon dioxide may be supplied to the trench by a wide variety of methods. In a preferred embodiment, the carbon dioxide-rich gas produced in treating the waste is held in a storage facility 230 (schematically depicted as a building in FIG. 1) and is delivered to the trench through conduit means 232. If more than one trench is formed at the site, the conduit means 232 may include a manifold 234 for controllably distributing the gas to each of the trenches.

The conduit means may deliver the carbon dioxide-rich gas in essentially "pure" form. However, as explained above, carbon dioxide can be toxic to animal life at a concentration of about 10%. If such highly-concentrated carbon dioxide gas were to be delivered into the trench 210, this would create a gradient of carbon dioxide concentration along the length of the trench as the gas mixes with ambient air, and may present toxic levels of carbon dioxide adjacent the conduit means. It is preferable, therefore, to deliver an admixture of the carbon dioxide-rich gas and air at higher volumes to achieve the desired concentration within the trench. Both the flow rate and the concentration of carbon dioxide in this carbon dioxide-rich gas supply may be varied according to known principles in order to effectively ensure that the desired concentration is achieved, and that the carbon dioxide concentration is substantially constant along the length of the trench.

In one preferred embodiment, the conduit means includes a spur 236 which extends between the manifold 234 and a position adjacent the first end of the trench. This spur may simply discharge the carbon dioxide-rich gas directly into the trench, but it is preferred that a series of baffles (not shown) or the like be provided adjacent the discharge end of the spur to more effectively spread the gas supply across the floor of the trench. Alternatively, each trench may be supplied by a plurality of spurs 236 which are spaced horizontally across the width of the floor 212 of the trench. If conduit means according to the present embodiment are utilized, it is desirable that the floor of the trench slope generally downwardly in a direction away from the spur 236, as noted above. Since carbon dioxide is heavier than air, this will lead to a more uniform distribution of carbon dioxide along the length of the trench because the carbon dioxide will tend to flow downhill, i.e., away from the spur 236. If so desired, this tendency may be enhanced by increasing the density of the gas exiting the spur, such as by cooling the gas by maintaining it under relatively high pressures in the conduit means 232.

In another preferred embodiment, the spur 236 of the previous embodiment is replaced with a supply duct 238 which may extend along substantially the entire length of the trench 210. The supply duct may be provided with a number of discharge ports (not shown) which are substantially equally spaced along the length of the supply duct to more evenly distribute the carbon dioxide-rich gas along the length of the trench. If the trench 210 includes a ditch (218 in FIG. 14), the supply duct 238 may rest in such a ditch. If so desired, more than one supply duct 238 may be provided in a trench, but it is not believed that this will be necessary under normal circumstances.

Thus, the present invention provides an efficient, cost-effective method of transporting, treating, and utilizing a flowable waste material. This method is particularly useful in connection with a strip-mining operation. Waste ca be transported from a city or the like to the strip mining site at very low cost because the train hauling coal from the mine to the city would otherwise have to deadhead from the city to the mine. A large-scale treatment facility utilizing anaerobic digestion can be located at the mine site, where land value tends to be significantly less than in metropolitan areas. Finally, the products of this large scale anaerobic digestion can be used as a fuel source and to assist in reclamation of the strip-mining site by enhancing the growth of commercially valuable plants in trenches already present at the site.

While a preferred embodiment of the present invention has been described, it should be understood that various changes, adaptations and modifications may be made therein without departing from the spirit of the invention and the scope of the appended claims.

What is claimed is:

1. A method of handling waste, comprising:
    a) providing transport means have a material-receiving cavity and a waste-receiving bladder carried within a portion of the cavity;
    b) loading a flowable waste material into the bladder at a waste collection site;
    c) transporting the waste material to a treatment facility, the treatment facility being located remotely of the collection site;
    d) unloading the waste material from the bladder and delivering the waste to the treatment facility;
    e) filling a portion of the material-receiving cavity of the transport means with a non-waste material; and
    f) transporting the non-waste material to a drop-off site located remotely of the treatment facility.

2. The method of claim 1 wherein the drop-off site is located relatively closely to the waste collection site, further comprising the step of transporting the transport means a relatively short distance from the drop-off site to the waste collection site.

3. The method of claim 1 wherein the material-receiving cavity has an open top, further comprising the steps of
    collapsing the bladder into a generally flat shape, and utilizing the bladder as a tarpaulin to cover non-waste material retained within the material receiving cavity.

4. The method of claim 1 further comprising the step of substantially removing the bladder from the material receiving cavity to permit the cavity to be unobstructedly filled with said non-waste material.

5. The method of claim 4 wherein the bladder is collapsible, the step of substantially removing the bladder comprising collapsing the bladder and spirally rolling the bladder.

6. The method of claim 1 further comprising the step of anaerobically digesting the waste to produce a biogas containing carbon dioxide.

* * * * *